United States Patent [19]
Hagiwara

[11] Patent Number: 5,442,189
[45] Date of Patent: Aug. 15, 1995

[54] APPARATUS FOR INSPECTING DEFECTS AND FOREIGN SUBSTANCES HAVING A SPOT ILLUMINATED FOCUSING SYSTEM

[75] Inventor: Tsuneyuki Hagiwara, Kawasaki, Japan

[73] Assignee: Nikon Corporation, Tokyo, Japan

[21] Appl. No.: 124,461

[22] Filed: Sep. 22, 1993

[30] Foreign Application Priority Data

Sep. 24, 1992 [JP] Japan .................................. 4-254590

[51] Int. Cl.6 ............................................ G01N 21/88
[52] U.S. Cl. ........................ 250/559.42; 356/237
[58] Field of Search ....................... 250/571, 572, 550; 356/394, 392, 237, 354; 382/31, 43, 48

[56] References Cited

U.S. PATENT DOCUMENTS

| | | | |
|---|---|---|---|
| Re. 33,956 | 6/1992 | Lin et al. | 250/550 |
| 3,614,232 | 10/1971 | Mathiseu | 250/572 |
| 4,806,774 | 2/1989 | Lin et al. | 250/550 |
| 4,845,356 | 7/1989 | Baker | 250/225 |

*Primary Examiner*—David C. Nelms
*Assistant Examiner*—Que T. Le
*Attorney, Agent, or Firm*—Shapiro and Shapiro

[57] ABSTRACT

An apparatus for inspecting defects and foreign substances on an object to be inspected comprises: an illumination optical system for illuminating a spot of illuminated area on a semiconductor wafer; a lens for executing Fourier transform of the patterns of said illuminated area; a spatial filter for blocking the components of the resultant Fourier transform images corresponding to the patterns having no defects; a lens for executing inverse Fourier transform of the light which is transmitted through the spatial filter to form images of the defect(s); and a photo detector array for receiving the images of the defect(s).

9 Claims, 12 Drawing Sheets

FIG. 1A
FIG. 1C
FIG. 1D
FIG. 1B
FIG. 1E
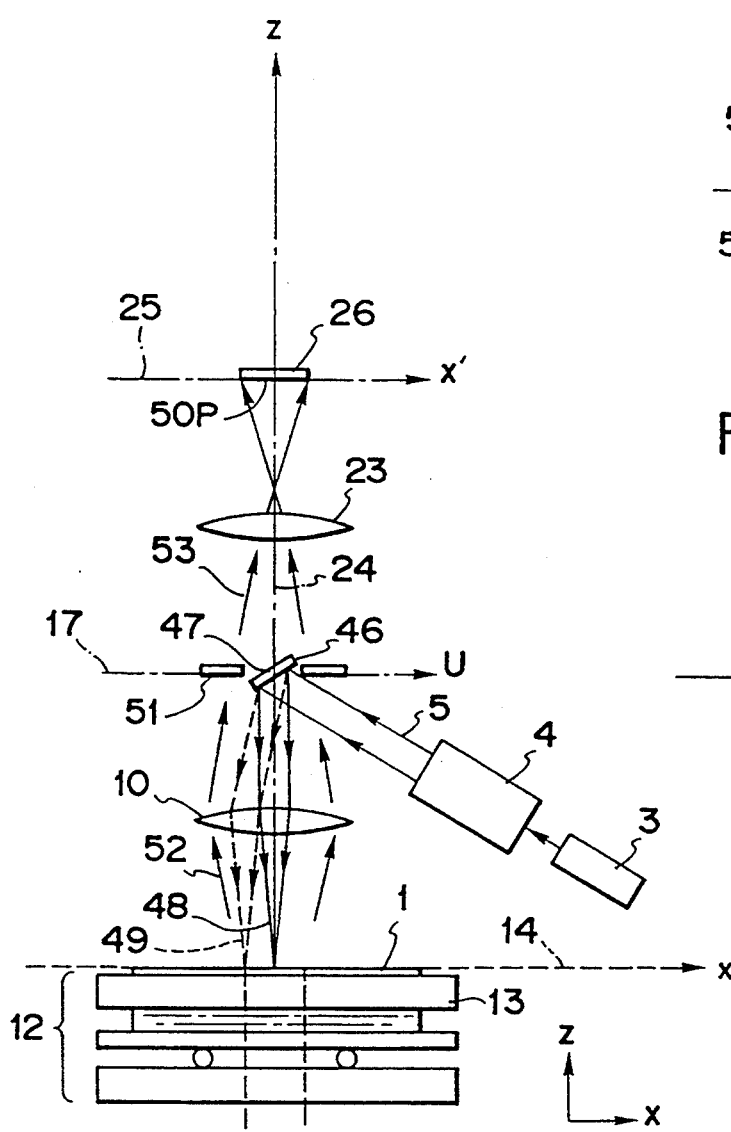
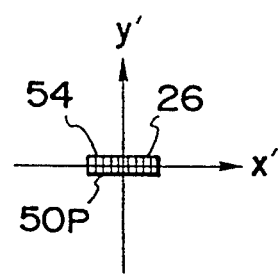
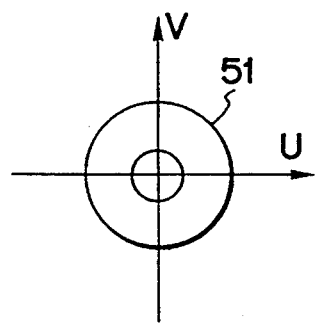
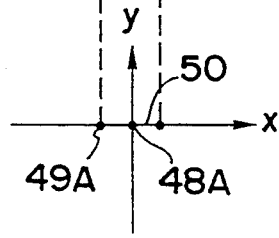
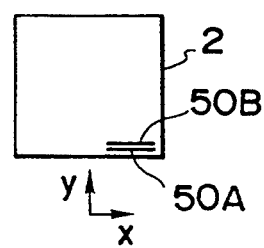

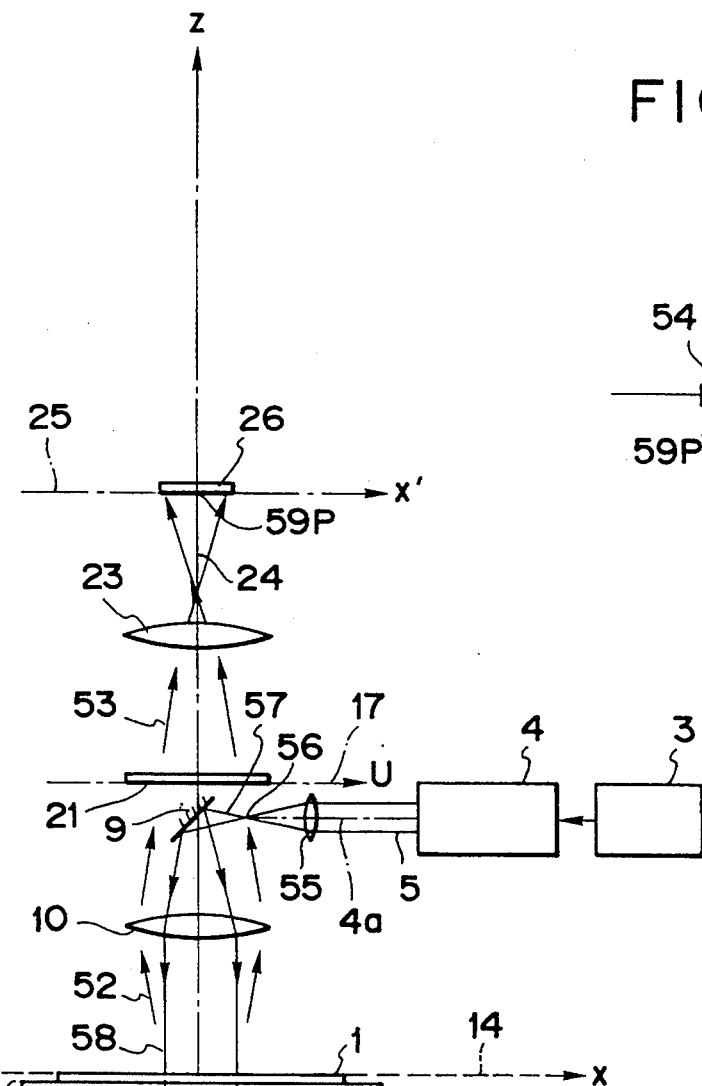
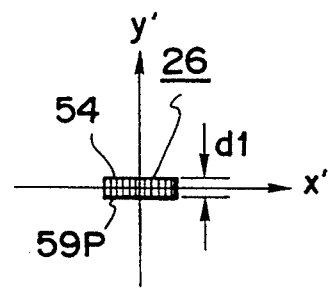
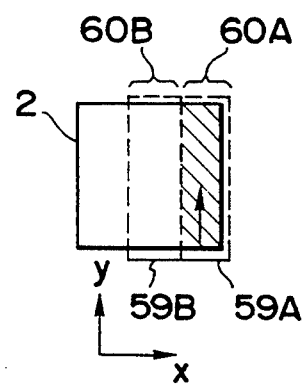
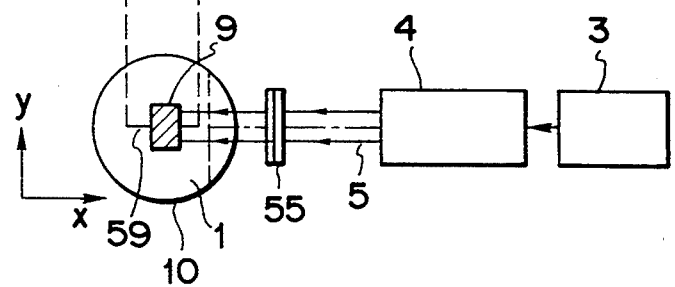

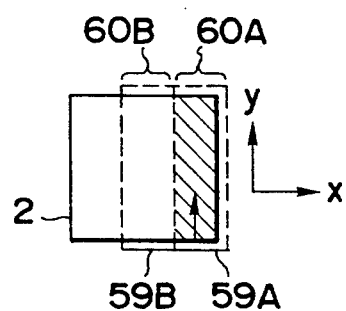
FIG. 4D
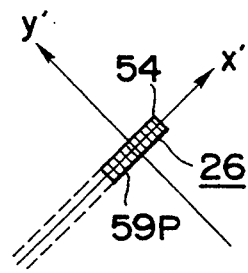
FIG. 4C
FIG. 4A
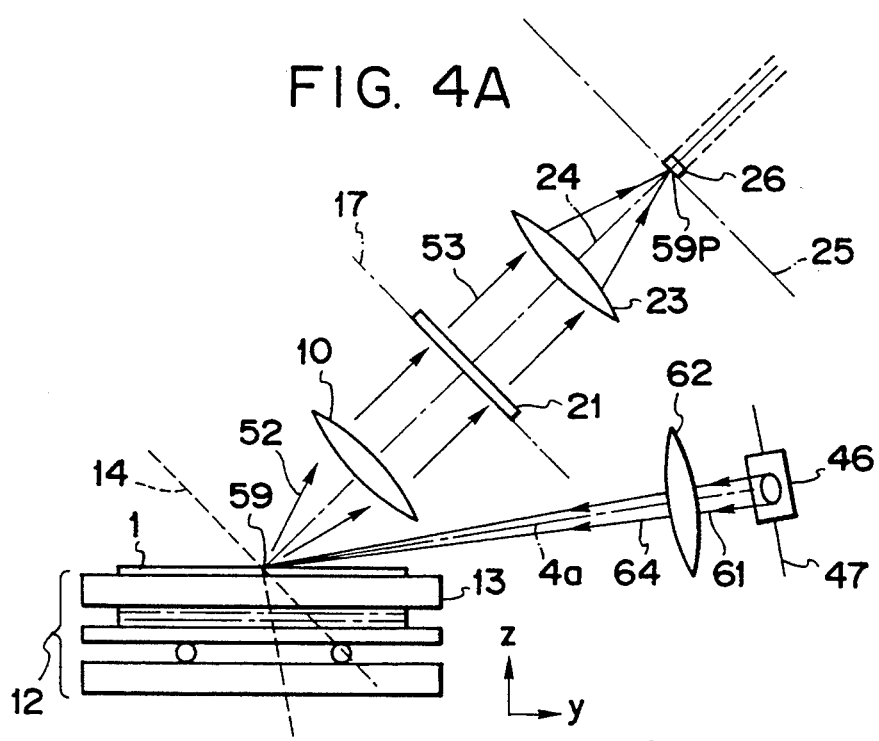
FIG. 4B
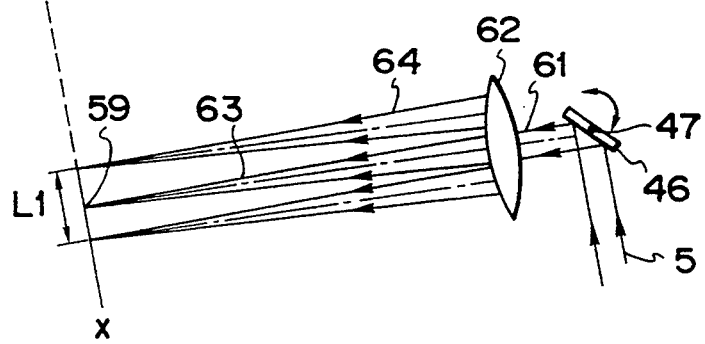

APPARATUS FOR INSPECTING DEFECTS AND FOREIGN SUBSTANCES HAVING A SPOT ILLUMINATED FOCUSING SYSTEM

BACKGROUND OF THE INVENTION

1. Field of the Invention

The present invention relates to an apparatus for inspecting defects and foreign substances, more specifically, to an apparatus which can be preferably used for inspecting defects in circuits on a reticle or a photomask used as an original plate in manufacturing a semiconductor element, and the like, or for inspecting defects, including foreign substances, on a substrate such as a semiconductor wafer.

2. Related Background Art

For example, in order to inspect defects in circuit patterns on a reticle or a photomask which is used as an original plate in manufacturing a semiconductor element, or in order to inspect foreign substances on a substrate such as a semiconductor wafer, an apparatus called "defect and foreign substance inspecting apparatus" has been used.

FIG. 5A shows such a typical defects and foreign substance inspecting apparatus, which is used for, for example, inspecting defects (including foreign substances) which are present in the periodical structure of a semiconductor wafer on which many circuit patterns are formed. FIG. 5C shows the semiconductor wafer 1 which is the object to be inspected. Generally, the semiconductor wafer 1 has a regular array of circuit units (hereinafter referred as "dies") 2, each of which has at least several tens of circuit patterns along both the X axis and the Y axis. A typical die 2 is a square of ca. 20 mm×20 mm.

The above-mentioned defect and foreign substance inspecting apparatus is disclosed in U.S. Ser. No. 060090, filed on Jun. 8, 1987.

As shown in FIG. 5A, the inspecting apparatus has a laser light source 3. A monochromatic laser beam emitted from the laser light source 3 is converted into a substantially collimated beam 5 having a predetermined diameter by a beam expander 4. The beam 5 is focused at a focal point 7 in a rear focal surface of a lens 6 by the lens 6. A beam 8 diverging from the focal point 7 is reflected by a reflecting mirror 9 arranged in the vicinity of the focal point 7. The beam reflected by the reflecting mirror 9, which has a circular cross section, travels towards a Fourier transform lens 10.

The effective center of the lens 10 is arranged to be at a position a little nearer than the focal distance of the lens 10. A collimated beam 11 emitted from the lens 10 is incident on the surface of the semiconductor wafer on which the patterns are formed. The semiconductor wafer 1 is held in a chuck 13 which is a part of a two-dimensional parallel displacement means 12. The two-dimensional parallel displacement means 12 can displace the semiconductor wafer 2 two-dimensionally in a plane vertical to the optical axis of the lens 10. The semiconductor wafer 1 is arranged in an object surface (that is, the front focal surface) of the lens 10 so that the surface of the semiconductor wafer 1 on which the patterns are formed is illuminated with the collimated beam 11.

As shown in FIG. 5B, an illuminated area 15 having a diameter of 20 mm in the surface of the semiconductor wafer 1 is illuminated with the collimated beam 11. As shown in FIG. 5A, a beam 16 diffracted by the illuminated area of the semiconductor wafer 1 is led through the lens 10 to a Fourier transform plane (that is, the rear focal surface) 17 of the lens 10, on which the image of the Fourier transform pattern corresponding to the circuit patterns in the illuminated area on the surface of the semiconductor wafer 1 is formed.

Incidentally, if the reflecting mirror 9 employed in the optical system shown in FIG. 5A is a half mirror, and if the semiconductor wafer 1 does not have any circuit patterns, that is, no circuit patterns have not yet been formed, the constitution of the apparatus in the vicinity of the reflecting mirror 9 shown in FIG. 5A is replaced by a corresponding constitution shown in FIG. 6. In the inspecting apparatus shown in FIG. 6, the diameter of the beam spot focussed at the rear focal point 7 of the lens 6 is in inverse proportion to the diameter of the monochromatic collimated beam 5 emitted from the beam expander 4 towards the lens 6. The beam 8 diverging from the focal point 7 travels towards a half mirror 18, and the beam, which has a circular cross section, reflected by the half mirror 8 travels towards the lens 10. The collimated beam 11 emitted from the lens 10 is reflected by a wafer 1A having no circuit pattern, is transmitted through the lens 10 again to be a beam 19, and the beam 19 forms a beam spot 20 on the Fourier transform plane 17 of the lens 10. The diameter of the beam spot 20 is substantially the same as that of the beam at the focal point 7.

To return to FIGS. 5A and 5C, the illuminated area 15 on the semiconductor wafer 1 having the diameter of 20 mm gives sufficiently exact Fourier transform patterns. For, the semiconductor wafer 1 has a lot of circuit patterns.

A previously prepared spatial filter 21 is provided in the Fourier transform plane (the rear focal surface) 17 of the Fourier transform lens 10. The spatial filter 21 can be prepared by exposing a recording medium such as a photographic dry plate to the light diffracted by all the dies on the semiconductor wafer 1. The semiconductor wafer 1 used here may be the very semiconductor wafer to be inspected even if some patterns of said semiconductor wafer 1 have defects. For only the Fourier transform beams informing the normal patterns of the semiconductor wafer 1 can expose the photographic dry plate with relatively high intensity, while the relatively weak beams informing the defects can not.

Therefore, the spatial filter 21 blocks the spatial frequency of the non-defective Fourier transform information of the illuminated dies 2 on the semiconductor wafer 1, but transmits the beams generated by the defects in these dies 2. A beam 22 conveying the defect information which is not blocked by the spatial filter 21 is incident on an inverse Fourier transform lens 23. Though the lens 23 is illustrated as a single lens in the drawing, the lens 23 may consists of a plurality of lens elements. The lens 23 is arranged at a position away from the Fourier transform plane 17 of the lens 10, wherein the distance between the lens 23 and the Fourier transform plane 17 is the same as the focal distance of the lens 23. The lenses 10 and 23 are aligned along the same optical axis 24. The two-dimensional parallel displacement means 12 displaces the semiconductor wafer 1 in the direction vertical to the optical axis 24. The lens 23 performs the inverse Fourier transform of the filtered light patterns of the illuminated dies 2 on the semiconductor wafer 1 and forms the images of the defective dies 2 in the rear focal surface, that is, the image surface 25 of the lens 23.

A photo detector array 26 is arranged in the rear focal surface of the lens 23, that is, on the image surface 25 on which the images of the defects are formed so that the center of the photo detector array 25 coincides with the optical axis 24. Each light-receiving element of the photo detector array 26 receives images of the defects present in the dies 2 on the optical axis 24.

According to the above-mentioned conventional art, the Fourier transform lens 10 and the inverse Fourier transform lens 23 should be designed on highly exacting conditions in order to sufficiently reduce electronic or optical noises.

In order to sufficiently reduce optical noises, the minimum spot diameter d1 on the Fourier transform plane 17 and the minimum spot diameter d2 on the image surface are strictly limited. On the other hand, in order to sufficiently reduce electronic noises, the lenses 10 and 23 have to be able to collimate the beams diffracted into space defined as a circular cone which is telecentric more than ±15° from any positions in the field of view in the object surface (the front focal surface) 14 of the lens 10 with sufficiently little aberration, and have to finally form images of paraxial diffracted beams with very little geometrical distortions.

In order to satisfy the above-mentioned condition, as shown in FIGS. 5B and 5C, the observable field 27 in which the defects can be inspected with sufficiently little electronic or optical noises should be smaller than the illuminated area 15 on the semiconductor wafer 1. The size of the illuminated area is determined so as to realize the optimal exposure of the spatial filter 21, and the entire illuminated area 15 must be illuminated even when only the observable field 27 is observed. For the Fourier transform patterns of the circuit patterns in the illuminated dies 2 at the time of the preparation of the spatial filter 21 needs to be the same as the Fourier transform patterns at the time of the defect inspection operation.

In order to explain the above situation, suppose an inspecting apparatus which illuminates as large an area as the observable field 27 shown in FIG. 5B. That is, as shown in FIG. 7, a collimated beam 29 with a small diameter which is emitted from the Fourier transform lens 10 illuminates only the observable field. In this case, the non-observable reagion in the illuminated area 15 which is indicated by slant lines in FIG. 5B does not have to be illuminated. But, as shown in FIG. 7, the diameter of a beam spot 31 formed in the Fourier transform plane 17 by a reflected beam 30 from the wafer 1A without circuit patterns is greater than the diameter of the beam spot 20 formed in FIG. 6, so the beam spot 31 can not be completely shielded by the spatial filter in the Fourier transform plane 17. Therefore, the entire illuminated area 15 has to be illuminated also at the time of the defect inspection operation, which makes it difficult to illuminate the observable field 27 with illumination light having sufficient illuminance.

In addition, the illuminance of the illumination light with which the observable field 27 shown in FIG. 5C is illuminated affects the time required for inspection. Since the observable field is not large enough to observe a whole die 2 on the semiconductor wafer 1 at the same time, the observable field 27 should be shifted within the die 2. The velocity of relative displacement of the observable field 27 with respect to the die 2 is determined according to the light cumulative time of the photo detector array 26 and the illuminance of the light with which the observable field is illuminated, wherein the lower the illuminance becomes the smaller the velocity of relative displacement will be, of course. Incidentally, when a light cumulative method such as time delay integration (TDI) is employed by the photo detector array 26, as is sometimes the case, highly exact operation of relative displacement is required.

In order to sufficiently reduce electronic or optical noises according to the above-mentioned conventional art, the Fourier transform lens 10 and the inverse Fourier transform lens 23 should be designed on highly exacting conditions. In addition, it is difficult to illuminate the observable field 27 with illumination light having sufficient illuminance. Therefore, according to the conventional art, charge storage photo detector elements are used in the photo detector array 26 and technique such as the time delay integration (TDI) is employed which synchronize the relative displacement of the observable field 27 on the semiconductor wafer 1 to be inspected with charge storage in the photo detector array 26 and charge shift within picture elements. When such technique is employed, however, highly exact operation of relative displacement of the object to be inspected is required, which is very difficult.

The above difficulties rise because the substantially collimated beam is used as the illumination light with which the object to be inspected is illuminated.

SUMMARY OF THE INVENTION

In consideration of the above-mentioned problems, an object of the present invention is to provide an apparatus for inspecting defects and foreign substances which can not only illuminate the observable field of the object to be inspected with illumination light having sufficient illuminance but also reliably shield the components of the Fourier transform corresponding to the normal patterns by means of the spatial filter in order to inspect the defects with sufficiently little optical or electronic noises.

The defect and foreign substance inspecting apparatus according to the present invention, as shown in FIGS. 1A to 1E, for example, comprises: a first lens for optically forming Fourier transform images of patterns to be inspected; a second lens for inverse Fourier transform of said Fourier transform images and projecting the image of the defects in the inspected patterns; an illumination means for illuminating a spot of the illuminated area or a linear illuminated area in the inspected patterns; an optical filter means for removing the components corresponding to the inspected pattern without defects from the optical images of the Fourier transform of the inspected patterns; a photoelectric detection means for photoelectrically converting the images of the defects in the inspected patterns projected by the second lens; and a relative displacement means for displacing the patterns to be inspected relatively with respect to the illumination means.

In said apparatus, the illumination means illuminates the area on the patterns to be inspected around the optical axis of the first and the second lenses, and the light receiving surface of the photoelectric detector means is preferably arranged at the conjugate point with respect to said area on the patterns to be inspected around the optical axis.

Also, the area of the light-receiving surface of the photoelectric detector means is preferably smaller than the area of the smallest image of the defects to be inspected in the inspected patterns, which is projected by the second lens.

Further, the area of the light-receiving surface of the photoelectric detector means may be substantially the same as the area of the conjugate image, which is formed by the first and the second lenses, of the illuminated area on the inspected patterns illuminated by the illumination means.

In addition, for example, as shown in FIGS. 3A to 3D, the optical axis of the first and the second lenses may be arranged so as to slantingly cross, on the patterns to be inspected, the optical axis of the illumination means.

While a conventional apparatus illuminates the patterns to be inspected with a substantially collimated beam, the present invention illuminates the patterns to be inspected with a focussed beam. Accordingly, the optical axis of the first and the second lenses and the optical axis of the illumination means do not have to be vertical to the surfaces of the patterns to be inspected and electronic or optical noises can be considerably reduced.

The reason why the present invention reduces the electronic or optical noises will be described below in detail. FIGS. 8A to 8C show some examples of the patterns of die circuits (circuit units) to be inspected. Suppose these die circuit patterns are larger than the illuminated area in the following description. First, the Fourier transform patterns on the Fourier transform plane 17 obtained by executing the Fourier transform of the patterns shown in FIGS. 8A to 8C by means of the conventional optical system shown in FIG. 6 is considered. In this case, the image heights U and V in the Fourier transform plane 17 depend on spatial frequencies u and v as follows.

Suppose a rectangular coordinate system with a U-axis and a V-axis in the rear focal surface (the Fourier transform plane) of the Fourier transform lens 10 so that the origin coincides with the intersection of the optical axis 24 and the rear focal surface 17. The U-axis and the V-axis indicate the dimensions of the images formed by the Fourier transform lens 10. In this case, the Fourier transform lens 10 has characteristics as expressed in the following equations (1) and (2)

$$U = f \sin\theta x = fl \quad (1)$$

$$V = f \sin\theta y = fm \quad (2)$$

wherein f: focal distance of the lens 10, $\theta x$: x-component of the angle of field, $\theta y$: y-component of the angle of field, l: direction cosines of diffracted beams (components parallel to the X-axis), m: direct cosines of diffracted beams (components parallel to the Y-axis).

On the other hand, Fourier transform information is generally given in a rectangular coordinate system of the spatial frequencies u and v, wherein the relations below exist by the definition of the Fourier transform:

$$u = (l - l_0)/\lambda \quad (3)$$

$$v = (m - m_0)/\lambda \quad (4)$$

wherein respective variables area defined as follows.
l: direction cosines of diffracted beams (components parallel to the X-axis)
$l_0$: direction cosine of the 0th-order diffracted beam (component parallel to the X-axis)
m: direct cosines of diffracted beams (components parallel to the Y-axis).

$m_0$: direct cosine of the 0th-order diffracted beam (component parallel to the Y-axis)

The position of the 0th-order diffracted light in the U-V plane is given by $U_0$ and $V_0$, which are expressed as in the equations (5) and (6) below:

$$U_0 = fl_0 \quad (5)$$

$$V_0 = fm_0 \quad (6)$$

From the above equations (1) to (6), the following relations are obtained:

$$u = (U - U_0)/\lambda f \quad (7)$$

$$v = (V - V_0)/\lambda f \quad (8)$$

These equations (7) and (8) shows that spectral distribution of the rectangular coordinates of the spatial frequencies u and v subjected to analogy convention with a coefficient $\lambda f$ is observed on the U·V plane with the origin ($U_0$, $V_0$).

The Fourier transform patterns of the die circuit patterns in FIG. 8A are shown in FIG. 9A. In this case, if the coordinate axes are referred as the X-axis and the Y-axis, the X-axis and the Y-axis and parallel to the U-axis and the V-axis, respectively. And according to the equations (7) and (8), we can say, when $\lambda f = 1$, as follows.

For example, in the X-Y plane shown in FIG. 8A, the die circuit patterns 32 have a pitch Px in the X direction and a pitch Py in the Y direction. In this case, in the U-V plane shown in FIG. 9A, the corresponding Fourier transform patterns 32A have a pitch 1/Px in the U direction and a pitch 1/Py in the V direction.

The die circuit patterns 33 shown in FIG. 8B have a pitch Pa in a periodical direction a and a pitch Pb in another periodical direction b. The corresponding Fourier transform patterns 33A in the U-V plane shown in FIG. 9B have periodical directions a' and b' vertical respectively to the periodical directions a and b, wherein the pitch in the direction a' is 1/Pa and the pitch in the direction b' is 1/Pb. Similarly, as the die circuit patterns 34 shown in FIG. 8C have a pitch Pc in a periodical direction c and a pitch Pd in another periodical direction d, the corresponding Fourier transform patterns in the U-V plane shown in FIG. 9C have periodical directions c' and d' vertical respectively to the periodical directions c and d, wherein the pitch in the direction c' is 1/Pc and the pitch in the direction d' is 1/Pd.

In FIG. 6, if the wafer 1A on which circuit patterns have not been formed yet is set on the object surface (the front focal surface) of the Fourier transform lens 10, the beam spot 20 formed on the Fourier transform plane 17 is bright. In this case, the beam spot 20 corresponds to the Fourier transform pattern of the collimated beam 11.

FIG. 11 shows the result of conversion of the pattern on the Fourier transform plane in the case shown in FIG. 6 into a pattern in the U-V plane. As shown in FIG. 11, the beam spot 20 shown in FIG. 6 is converted into a bright spot 20A in the U-V plane. This beam spot 20A and the beam spots 20A constituting the Fourier transformation patterns 32A to 34A in the U-V planes shown in FIGS. 9A to 9C are congruent.

FIG. 10 shows an example of the optical system in an embodiment of the present invention. In FIG. 10 a collimated beam 35 emitted from the beam expander 4 is reflected by the half mirror 18 towards the Fourier transform lens 10. The wafer 1A without circuit patterns is illuminated with a beam spot 36A of a focussed beam 36 emitted from the lens 10. The surface of the wafer 1A is positioned in the object surface 14 of the lens 10, and a beam spot 37, which is the Fourier transform patterns corresponding to the beam spot 36A, is formed on the Fourier transform plane 17, which is the rear focal surface of the lens 10. That is, the reflected light beam from the wafer 1A without circuit patterns is transmitted through the lens 10 and the half mirror 18, and is incident as the collimated beam 37 on the Fourier transform plane 17. The cross-section of the beam 37 in the Fourier transform plane 17 is the beam spot 38.

In this case, the beam spot 31A and the beam spot 38A in the U-V plane shown in FIG. 11 correspond respectively to the beam spot 31 in the optical system shown in FIG. 7 and the beam spot 38 in the optical system shown in FIG. 10, both of which are formed on the Fourier transform plane 17 when the wafer 1A without circuit patterns is set on the object surface 14 of the lens 10. The beam spot 31A corresponds to the Fourier transform pattern of the collimated beam 29 used as illumination light, while the beam spot 38A corresponds to the Fourier transform pattern of the focussed beam 36 used as illumination light. Accordingly, though the center position of the beam spot of the Fourier transform pattern generated when the die circuit patterns shown in FIGS. 8A to 8C are illuminated by the optical system shown in FIG. 7 or FIG. 10 is the same as the center position of the Fourier transform patterns 32A to 34A shown in FIGS. 9A to 9C generated in the optical system shown in FIG. 6, these beam spots of the Fourier transform patterns corresponding to different illumination light beams have different sizes. Each of these Fourier transform patterns is obtained as convolution of the two-dimensional sequences of points (that is, the sequences of the lattice points in FIGS. 9A to 9C) indicating the center positions of the beam spots and the beam spots (Fourier spectra) 20A, 31A and 38A of respective illumination light beams in the U-V plane shown in FIG. 11.

More specifically, FIGS. 12A to 12C respectively show the Fourier transform patterns 32B, 33B and 34B generated by illuminating the die circuit patterns in FIGS. 8A to 8C by means of the optical system shown in FIG. 10. The size of the beam spots 38A of the Fourier transform patterns 32B, 33B and 34B is the same as the size of the beam spot 3A shown in FIG. 11. Each of these Fourier transform patterns 32B, 33B and 34B is convolution of the two-dimensional sequences of points (the sequence of the lattice points in the patterns shown in FIGS. 9A to 9C) and the beam spot 38A shown in FIG. 11.

Next, a spot of illuminated area or a linear illuminated area in the patterns to be inspected is illuminated according to the present invention. Fourier transform patterns obtained from linear circuit patterns will be described.

FIGS. 13A to 13C respectively show linear circuit patterns 40, 41, 42 in an illuminated area 39. FIGS. 13D to 13F show the Fourier transform patterns 40A, 41A and 42A in the U-V planes having width of a1, corresponding to the linear circuit patterns shown in FIGS. 13A, 13B and 13C, respectively. The size of the illuminated area changes according to the optical systems employed, as shown in FIGS. 6, 7 and 10. For example, the Fourier transform pattern 40A has width a1 in the V direction which is the same as width of one of the Fourier transform patterns shown in FIG. 11 corresponding to respective illumination light beams. That is, the Fourier transform pattern 40A is convolution of the line coinciding with the U-axis and one of the Fourier transform patterns corresponding to respective illumination light beams shown in FIG. 11.

Next, the relation between the size of the illuminated area and the relative intensity of the light patterns obtained from the defects with respect to the intensity of the light patterns obtained from the circuit patterns will be considered.

FIG. 14 shows die circuit patterns 32 including a defect 45, in which the total amount of the illumination light in a large illuminated area 11A is supposed to be equal to the total amount of the illumination light in a small illuminated area 36A. In this case, we have a relation expressed as follows:

$$I = (i11A)(s11A) = (i36A)(s36A) \qquad (9)$$

wherein respective variables are defined as follows.
$i11A$ = luminance in the illuminated area 11A
$s11A$ = area of the illuminated area 11A
$i36A$ = luminance in the illuminated area 36A
$s36A$ = area of the illuminated area 36A
Note that as $s11A >> s36A$, $i11A << i36A$.

When the size of the defect 45 is denoted by ds, the amount of light with which the defect 45 is illuminated in the illuminated area 11A can be expressed as $i11A \cdot ds$. Similarly the amount of light with which the defect 45 is illuminated in the illuminated areas 36A can be expressed as $i36A \cdot ds$. Accordingly an equation below can be obtained:

$$(i11A)(ds) << (i36A)(ds) \qquad (10)$$

As is understood from the above equation (10), the smaller the illuminated area is, the greater the intensity of the light patterns obtained from the defect 45. The light patterns (the Fourier transform patterns) corresponding to the defect 45 can be obtained as "haze" all over the U-V plane. Now, the amount of light I (d20A) of the light patterns obtained from the defect(s) in an area d20A in the U-V plane shown in FIG. 9A and the amount of light I (d38A) of the light patterns obtained from the defect(s) in an area 38A in the U-V plane shown in FIG. 12A are exemplified. If both areas have the same size, since the amounts of light I (d20A) and I (d38A) are both in reverse proportion to the size of respective illuminated areas, the following operation is obtained;

$$I(d20A)/I(d38A) = S11A/S36A >> 1 \qquad (11)$$

On the other hand, the integrated values of the amount of light of the light patterns, obtained from the circuit patterns are the same, for the area ratios of the circuit patterns to respective illuminated areas are substantially the same. Also, the ratios of the amounts of light in respective beam spots in the U-V plane are constant regardless of the size of the illuminated areas. For example, if the ratio of the amount of light in the beam spot 43 in the patterns 32A shown in FIG. 9A to the amount of light in the beam spot 44 is 2:1, the ratio of the amount of light in the beam spot 43 in the patterns 32B shown in FIG. 12A to the amount of light in the beam spot 44 is also 2:1.

Therefore, as for the beam spots constituting the circuit patterns 32A in FIG. 9A and these constituting the circuit patterns 32B in FIG. 12A, the amounts of light in the beam spots corresponding to each other in the U-V plane are the same. For example, the amount of light in the beam spots 20A in FIG. 9A is the same as the amount of light in the beam spots 38A in FIG. 12A.

As the conventional defect and foreign substance inspecting apparatus uses collimated illumination light, only small amount of light of the light patterns corresponding to the defects can be obtained on the Fourier transform plane which blocks only the light patterns obtained from the normal circuit patterns. Therefore, the light patterns have to be filtered with high precision. In order to avoid such an inconvenience, the present invention makes the illuminated area smaller so that the distribution of transmissivity of the spatial filter arranged in the Fourier transform plane and the positioning of the spatial filter can be less precise.

According to the present invention, when the illumination means illuminates an area around the optical axis of the first and second lenses on the patterns to be inspected and the light-receiving surface of the photoelectric detection means is arranged at the conjugate point with respect to said area around the optical axis on the patterns to be inspected, the amount of light received by the photoelectric detection means increases to further reduce optical noises.

Also, when the size of the light-receiving surface of the photoelectric detection means is smaller than the size of the smallest image of the defects, which is the object to be inspected in the inspected patterns, projected by the second lens, the defect(s) can be inspected with higher resolving power than the smallest image of the defect(s).

Further, when the size of the light-receiving surface of the photoelectric detection means is substantially the same as the size of the conjugate image, which is formed by the first and second lenses, of the illuminated area on the inspected patterns illuminated by the illumination means, the light-receiving efficiency is excellent.

In addition, when, as shown in FIGS. 3A to 3D, for example, the optical axis of the first and second lenses is arranged to slantingly cross the optical axis of the illumination means on the surface of the inspected patterns, little amount of light diffracted by the normal patterns among the inspected patterns is incident on the first lens to further reduce optical noises.

According to the present invention, since the patterns to be inspected are illuminated with the focussed beam, not only the observed area of the object to be inspected can be illuminated with illumination light having sufficient illuminance, but also electrical and optical noises can be substantially reduced. Thus, the time required to execute inspection can be shortened. And the first lens serving as the Fourier transform lens and the second lens serving as the inverse Fourier transform lens can be designed on less exacting conditions (for example, with respect to aberration and performance). Also, as the spot of illuminated area or the linear illuminated area on the surface of the object to be inspected is illuminated with the focussed beam, both the optical axis of the light-receiving system and the optical axis of the illumination system can be slantingly arranged with respect to the surface of the object to be inspected, which can further reduce electronic and optical noises.

BRIEF DESCRIPTION OF THE DRAWINGS

FIG. 1A is a block diagram showing the first embodiment of the defect and foreign substance inspecting apparatus according to the present invention.

FIG. 1B is a plan view showing an illuminated area on a semiconductor wafer 1 shown in FIG. 1A.

FIG. 1C is a bottom view showing a photo detector array 26 shown in FIG. 1A.

FIG. 1D is a plan view showing a spatial filter 51 shown in FIG. 1A.

FIG. 1E is a plan view showing a die 2 or the semiconductor wafer 1 shown in FIG. 1A.

FIG. 2A is a block diagram showing the second embodiment of the defect and foreign substance inspecting apparatus according to the present invention.

FIG. 2B is a plan view showing a cylindrical lens 55, the illuminated area on the semiconductor wafer 1, and so on in FIG. 2A.

FIG. 2C is a bottom view showing the photoelectric detector array 26 shown in FIG. 2A.

FIG. 2D is a plan view showing the die 2 on the semiconductor wafer 1 shown in FIG. 2A.

FIG. 4A is a block diagram showing the fourth embodiment according to the present invention.

FIG. 4B is a diagram seen from the upside, showing an oscillation mirror 46, the illuminated area on the semiconductor wafer 1, and so on shown in FIG. 4A.

FIG. 4C is a diagram showing the photoelectric detector array 26 shown in FIG. 4C, which is seen from the side of the lens 23.

FIG. 4D is a plan view showing the die 2 on the semiconductor wafer 1 shown in FIG. 4A.

DESCRIPTION OF THE PREFERRED EMBODIMENTS

Figures 5A, 5B, 5C:
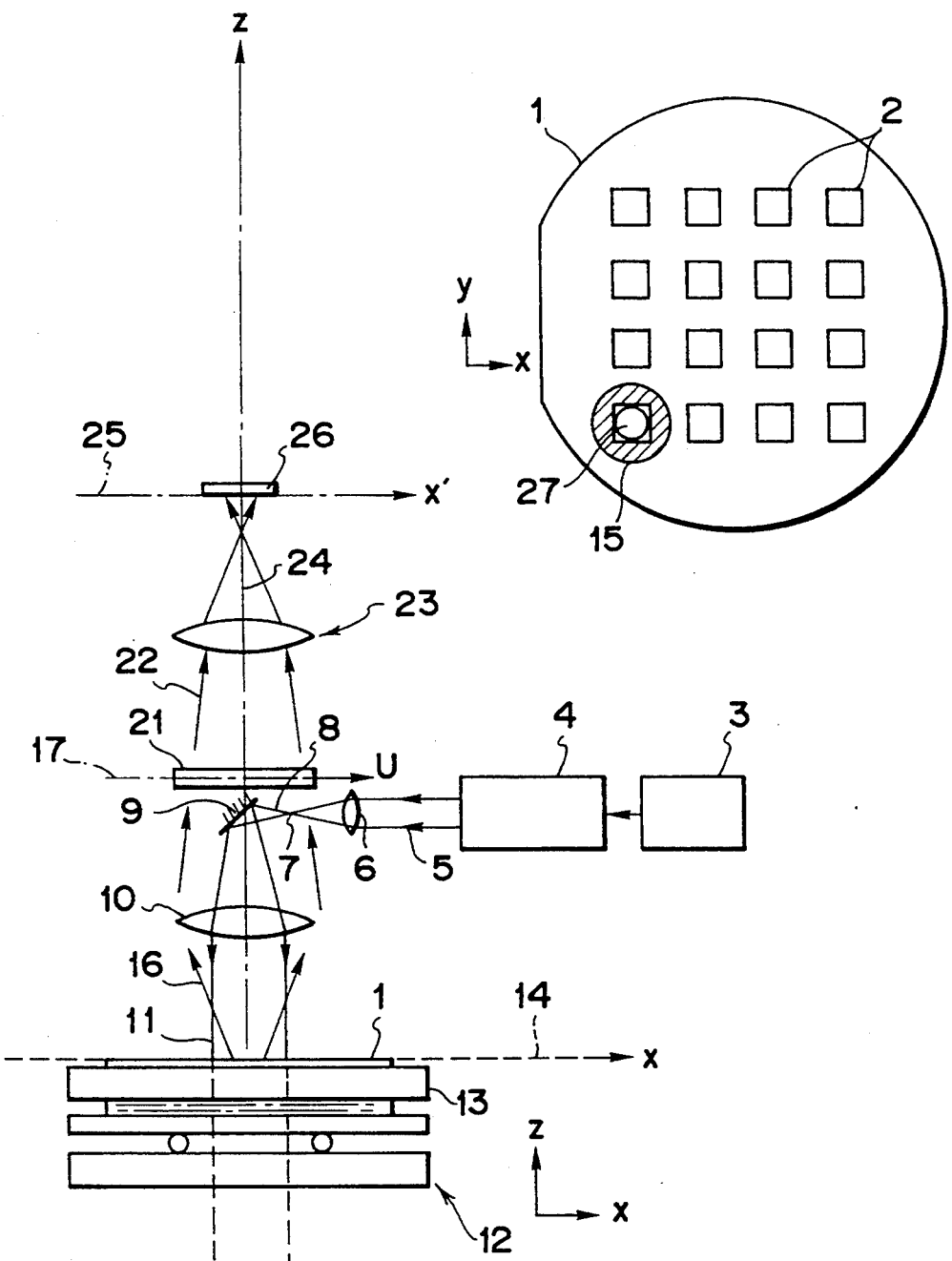
FIG. 5A is a block diagram showing a conventional defect and foreign substance inspecting apparatus.
FIG. 5B is a plan view showing the illuminated area on the semiconductor wafer 1 shown in FIG. 5A.
FIG. 5C is a plan view showing circuit patterns on the semiconductor wafer 1 shown in FIG. 5A.
Figure 6:
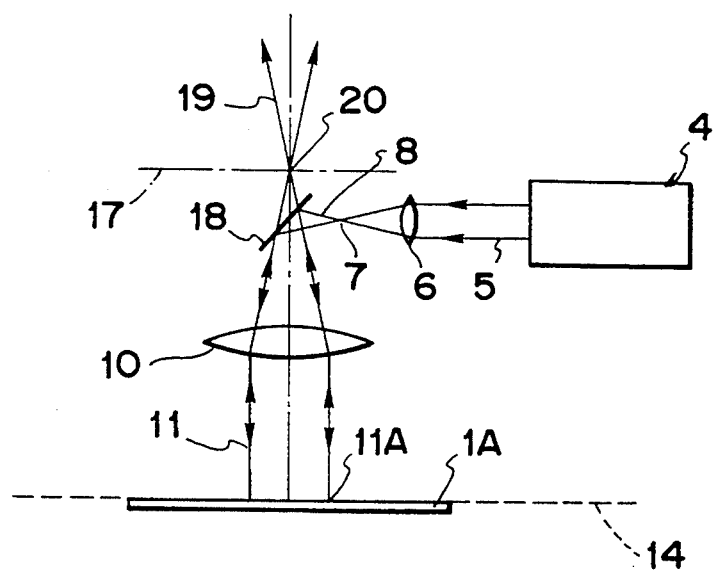
FIG. 6 is a block diagram showing main portions of another conventional defect and foreign substance inspecting apparatus.
Figure 7:
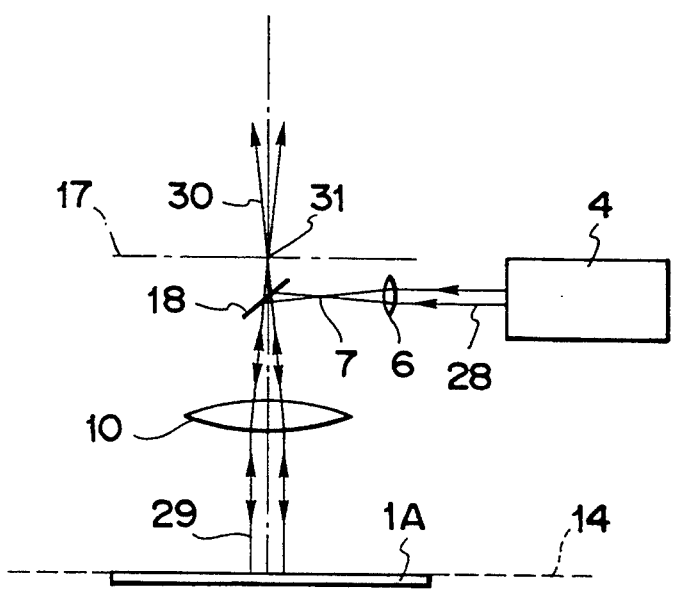
FIG. 7 is a block diagram showing main portions of the conventional defect and foreign substance inspecting apparatus, wherein the illuminated area is small.

Now, the first embodiment of the defect and foreign substance inspecting apparatus according to the present invention will be described with reference to FIGS. 1A to 1C. In this embodiment, the present invention is applied to an apparatus for inspecting defects in a periodical structure of a semiconductor wafer consisting of a lot of circuit patterns. In FIGS. 1A to 1E, components and portions corresponding to those shown in FIGS. 5A to 5C are indicated by the same reference numerals and detailed description thereof is omitted.

FIG. 1A shows the constitution of the embodiment of the defect and foreign substance inspecting apparatus, wherein a monochromatic laser beam from a laser light source 3 is converted by a beam expander 4 into a substantially collimated beam 5, which is casted on an oscillation mirror 46 arranged in the vicinity of the rear focal point of a Fourier transform lens 10. The beam 5 is reflected by the oscillation mirror 46 and travels towards the Fourier transform lens 10 as a beam having a circular cross section. Though the lens 10 is illustrated as a single lens, it consists of a plurality of lens elements.

The effective center of the lens 10 is arranged to be a position away from the surface of the semiconductor wafer 1 so that the distance between the effective center and the surface of the wafer 1 is the same as the focal distance. Thus, a focussed beam 48 emitted from the lens 10 is case on the surface of the semiconductor wafer 1. The semiconductor wafer 1 is held in a chuck 13 which is a part of a two-dimensional parallel displacement means 12. The surface of the semiconductor wafer 1 to be inspected is set in an object surface (the front focal surface) 14 of the lens 10, and the surface of the semiconductor wafer 1 on which patterns are formed is illuminated with the focussed beam 48. More specifically, a spot of illuminated area 48A on the semiconductor wafer 1 is illuminated with the focussed beam 48 (see FIG. 1B).

The oscillation mirror 46 is revolvably (to be oscillatory) supported around a shaft 47 in the vicinity of the Fourier transform plane (the rear focal surface) 17 of the lens 10. By oscillating the oscillation mirror 46 around the shaft 47, the focussed beam 48 can be shifted, for example, as indicated by reference numeral 49 which forms a spot of illuminated area 49A. Thus, as shown in FIG. 1A, the focussed beam 48 emitted from the lens. 10 continuously moves within an illuminated range 50, whose center is the spot of the illuminated area 48A on the surface of the semiconductor wafer 1 and whose length along the x-axis is L1. The x-axis and the y-axis in FIG. 1B are in the object surface (the front focal surface) 14 of the lens 10, and the origin thereof coincides with the optical axis 24. A beam 52 diffracted by the illumination range 50 on the semiconductor wafer 1 is transmitted through the lens 10, and forms the Fourier transform patterns corresponding to the illuminated region in the Fourier transform plane (the rear focal surface) 17 of the lens 10. A previously prepared spatial filter 51 is set in the Fourier transform plane 17. The oscillation mirror 46 is arranged in an opening at the center of the spatial filter 51. Accordingly, as shown in FIG. 1D, the spatial filter 51 is a zonal disc. The spatial filter 51 can be prepared by exposing a recording medium such as a photographic dry plate to light diffracted by all the dies 2 on the semiconductor wafer 1. The very semiconductor wafer 1 to be inspected can be used for preparing the spatial filter 51.

FIG. 1E shows a die (circuit unit) 2, which is the object to be examined, on the semiconductor wafer 1. In FIG. 1E, illuminated areas 50A, 50B, ... in the die 2 are scanned with the focussed beam in the x-direction by means of the oscillation mirror 46. And the long and narrow illuminated range 50 is scanned in the y-direction by shifting the semiconductor wafer 1 in the y-direction by the two-dimensional parallel displacement means 12. Thus, the entire region in the die 2 is raster-scanned with the focussed beam 48 as large as the corresponding spot of illuminated area 48A. Since the total intensity of the light patterns corresponding to the circuit patterns formed all over the die 2 is greater than the total intensity of the light patterns corresponding to the defect(s) amounting only a very little portion of the die 2, the photographic dry plate (the spatial filter 51 to be prepared) can be exposed only to light pattern information corresponding to the circuit patterns by giving an appropriate amount of exposure (which is determined as the speed of raster scanning operation multiplied by the amount of light in the illuminated areas).

In FIG. 1A, the spatial filter 51 blocks the components of the spatial frequency corresponding to the Fourier transform information of the dies 2 without defects (that is, the Fourier transform information obtained when defects do not exist), but transmits light generated by the defect(s) in the dies 2. A beam 53 which is not blocked by the spatial filter 51, that is, which carries the information about the defect(s) is incident on an inverse Fourier transform lens 23. Though the lens 23 is illustrated as a single lens, it consists of a plurality of lens elements. The lens 23 executes inverse Fourier transform of the filtered light patterns of the illuminated dies 2 on the semiconductor wafer 1. The lens 23 is positioned away from the Fourier transform plane (the rear focal surface) 17 of the lens 10, wherein the distance between the lens 23 and the Fourier transform plane 17 is the same as the focal distance of the lens 23. And the lenses 10 and 23 are aligned along the same optical axis 24. The two-dimensional parallel displacement means 12 shift the semiconductor wafer 1 so that the wafer 1 crosses the optical axis 24.

The images of the defect(s) present in the die 2 on the optical axis 24 are formed on the rear focal surface 25 that is, the images surface of the lens 23. The image of the defect(s) in the die 2 are received by the light-receiving surfaces of a one-dimensional photo detector array 26 provided around the optical axis 24 on the image surface 25. The one-dimensional photo detector array 26 consists of many light-receiving elements 54 (see FIG. 1C) which have respective photosensitive surface having width narrower than d2 and which are aligned one-dimensionally (in the X direction); wherein d2 is the diameter of a spot formed on the image surface 26 corresponding to the diameter of the spot d1 of the illuminated area 48a on the illuminated range 50. The number of the light-receiving elements 54 is determined so as to receive the entire line image 50P corresponding to the entire illuminated range on the semiconductor wafer 1 having length L1.

Figure 8A:
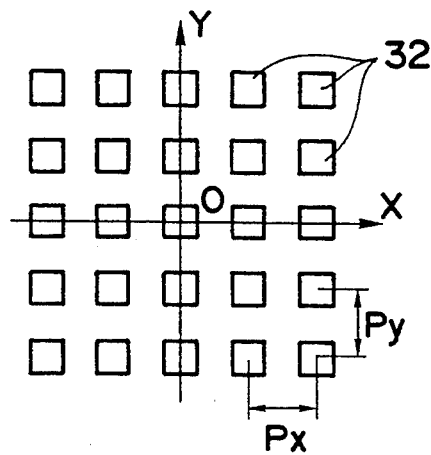
FIGS. 8A to 8C are plan views showing some examples of the die circuit patterns which are subjected to defect inspection.
Figure 8B:
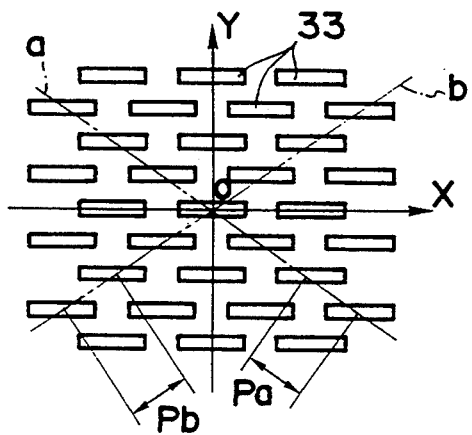
Figure 8C:
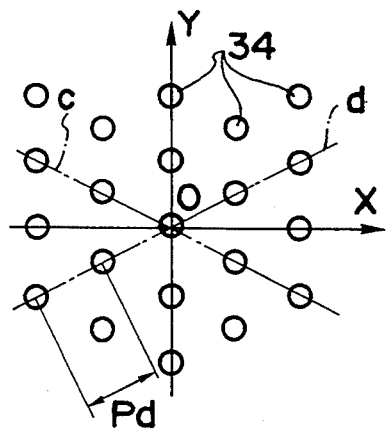
Figure 9A:
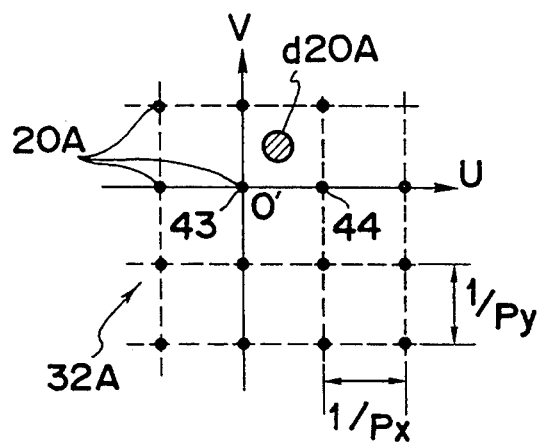
FIGS. 9A to 9C are plan views showing the Fourier transform patterns obtained by executing Fourier transform of the die circuit patterns shown in FIGS. 8A to 8C in the conventional defect and foreign substance inspecting apparatus.
Figure 9B:
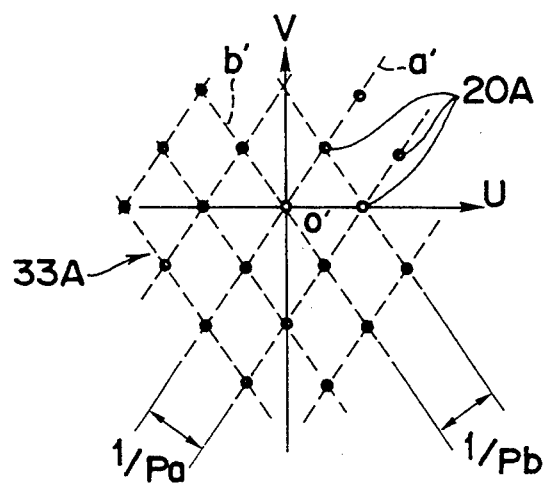
Figure 9C:
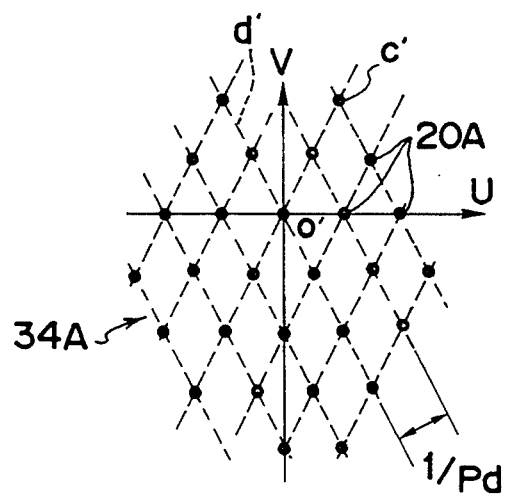
Figure 10:
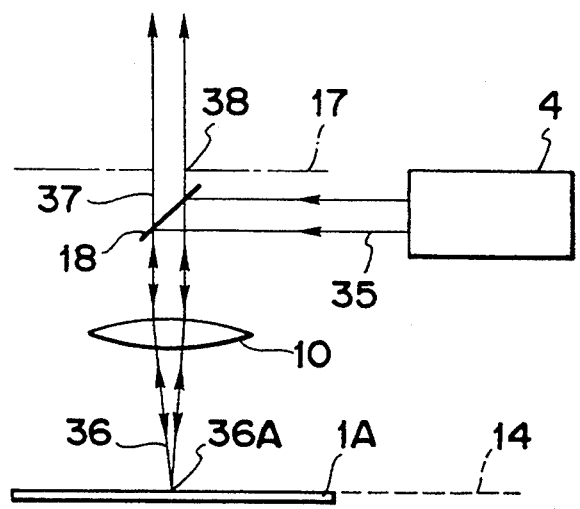
FIG. 10 is a block diagram showing main portions of an example of the defect and foreign substance inspecting apparatus according to the present invention.
Figure 11:
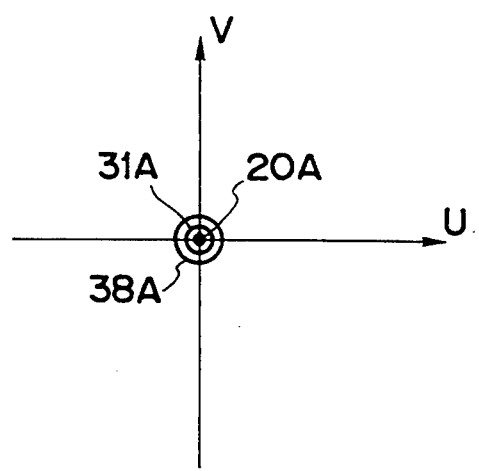
FIG. 11 is a plan view showing the Fourier transform patterns in the U-V plane obtained according to prior art and the present invention.
Figure 12A:
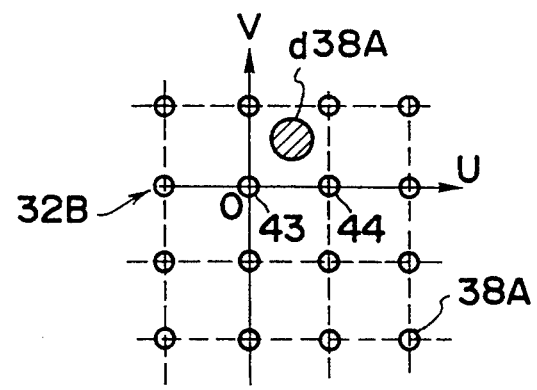
FIGS. 12A to 12C are plan views showing the Fourier transform patterns obtained by executing Fourier transform of the die circuit patterns shown in FIGS. 8A to 8C by means of the defect and foreign substance inspecting apparatus according to the present invention shown in FIG. 10.
Figure 12B:
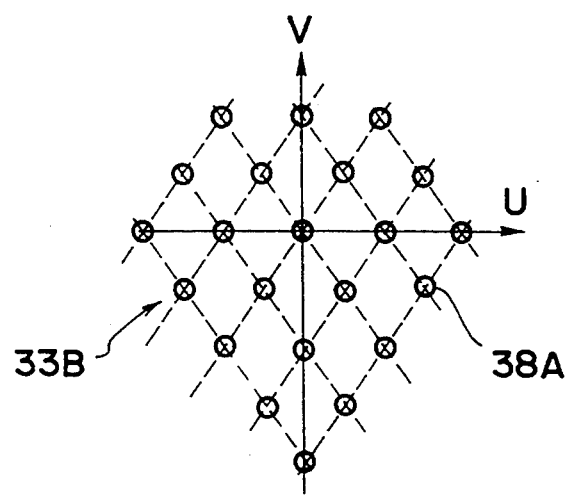
Figure 12C:
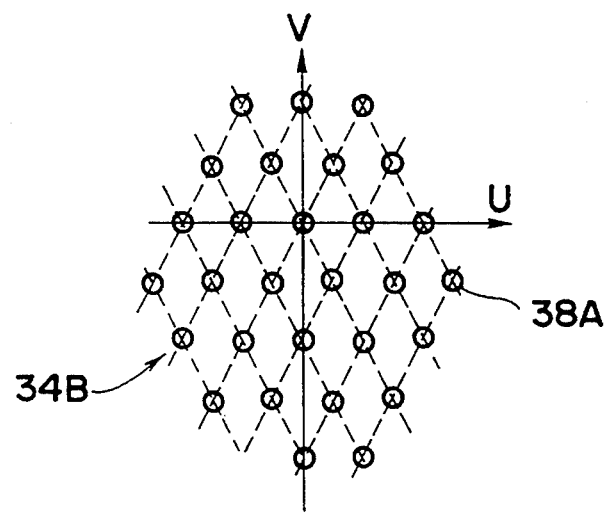
Figure 13A:
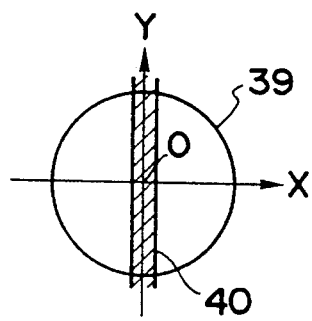
FIGS. 13A to 13C are plan view showing linear patterns in the illuminated areas on the semiconductor wafer.
Figure 13B:
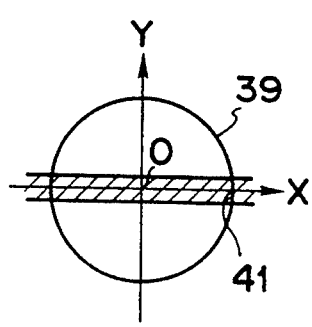
Figure 13C:
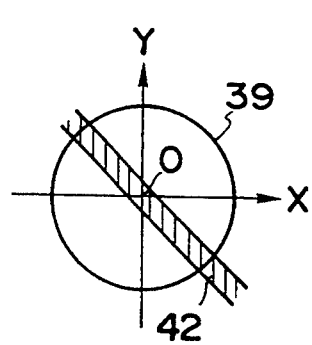
Figure 13D:
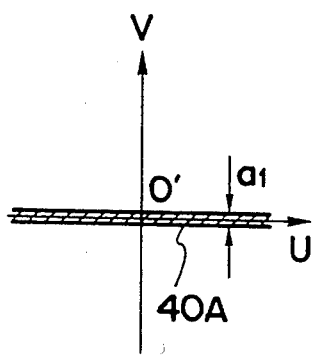
FIGS. 13D to 13F are plan views showing the Fourier transform patterns in the U-V plane corresponding to the linear patterns shown in FIGS. 13A to 13C, respectively.
Figure 13E:
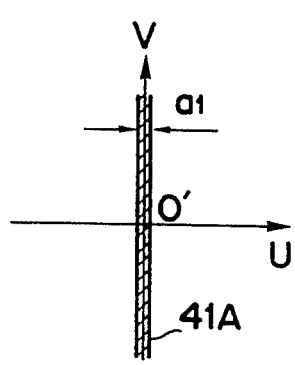
Figure 13F:
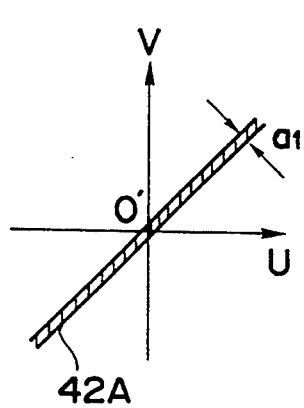
Figure 14:
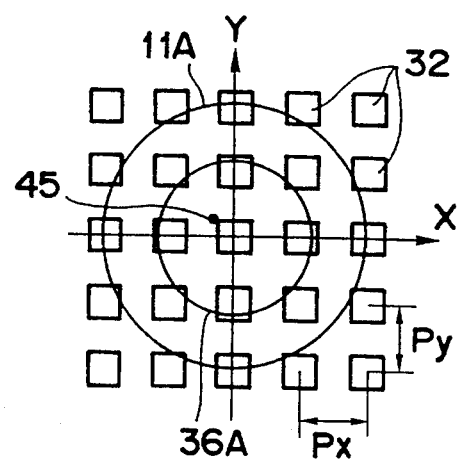
FIG. 14 is a plan view showing the die circuit patterns and a defect on the semiconductor wafer.

In the present embodiment, the Fourier transform patterns shown in FIGS. 12A to 12C, corresponding to the inspected die circuit patterns shown in FIGS. 8A to 8C, respectively, are formed on the Fourier transform plane 17. However, these normal Fourier transform patterns are blocked by the spatial filter 51, while the images of the defect(s) in respective dies 2 on the semiconductor wafer 1 can be displayed by two-dimensionally arranging the output signals from the photo detector array 26. In this case, as the semiconductor wafer 1 is illuminated with the focussed beam 48, electronic and optical noises are sufficiently reduced.

Next, the second embodiment of the present invention will be described with reference to FIGS. 2A to 2D; wherein components corresponding to those shown in FIGS. 1A to 1E and FIGS. 5A to 5C are indicated by the same reference numerals and detailed description thereof is omitted. FIG. 2A shows the second embodiments of the defect and foreign substance inspecting apparatus, in which the substantially collimated monochromatic beam 5 emitted from the beam expander 4 travels through an optical axis 4c and is incident on a cylindrical lens 55. The cylindrical lens 55 has power in the z direction parallel with the page space of FIG. 2A and vertical to the X-axis, but does not in the Y direction (vertical to the page space of FIG. 2A). The cylindrical lens 55 focuses the beam 5 on a focal line, which is part of the rear focal surface of the lens 55. The focal line is elongated in the y direction. A beam 57 diverging from the focal line 56 is reflected by a small reflecting mirror 9 provided rear the focal line 56 to be incident on the Fourier transform lens 10. Though the reflecting mirror 9 obstructs a very small area at the center of the Fourier transform plane of the lens 10, the information of the defect(s) formed on the rest of the Fourier transform plane 17 is not obstructed by the reflecting mirror 9.

The effective center of the lens 10 is arranged at a position away from the reflecting mirror 9 so that the distance between the reflecting mirror 9 and the effective center is a little smaller than the focal distance of the lens 10. Thus, a beam 58 emitted from the lens 10 is cast, as a beam focussed in the shape of a slit, on the surface of the semiconductor wafer 1 on which circuit patterns are formed. The surface of the semiconductor wafer 1 to be inspected is set in the object surface (the front focal surface) 14 of the lens 10, wherein a linear illuminated area 59 (see FIG. 2B) having length L1 on the surface of the semiconductor wafer 1 is illuminated with the beam 58. The beam 52 diffracted by the illuminated area 59 on the semiconductor wafer 1 is transmitted through the lens 10 and forms the Fourier transform patterns on the Fourier transform plane (the rear focal surface) 17 of the lens 10. A previously prepared spatial filter 21 is positioned in the Fourier transform plane 17.

In this embodiment, the entire die 2 on the semiconductor wafer 1 is illuminated as follows. As shown in FIG. 2D, first, a range 60A on the die 2 is scanned by relatively displacing the beam with which a linear illuminated area 59A is illuminated in the y direction by means of the two-dimensional parallel displacement means 12. Then, the beam is relatively displaced so that a linear illuminated area 59B is illuminated. And as described above, a range 60B is scanned by relatively displacing the beam with which the linear illuminated area 59B is illuminated in the Y direction. By repeating the above-mentioned operation, the entire die 2 is scanned with the linear beam with which the illuminated area 59 is illuminated.

When the spatial filter 21 is prepared, a photographic dry plate can be exposed only to light pattern information corresponding to the normal circuit patterns by giving an appropriate amount of exposure (which is determined as the speed of optical scanning multiplied by the amount of light in the illuminated areas). For, the total intensity of the light patterns obtained from the circuit patterns formed all over the dies 2 is greater than the total intensity of the light patterns corresponding to the defect(s) amounting only a very small portion of the dies 2.

The spatial filter 21 blocks the components of the spatial frequency corresponding to the Fourier transform information of the illuminated dies 2 on the semiconductor wafer 1 having no defects, but transmits light generated by the defect(s) in the dies 2. The beam 53 carrying the information of the defect(s) which is not blocked by the spatial filter 21 is incident on the inverse Fourier transform lens 23. The lens 23 executes the inverse Fourier transform of the filtered light patterns of the illuminated dies 2 on the semiconductor wafer 1 onto the object surface (the rear focal surface) 25.

Light-receiving surfaces of the one-dimensional photo detector array 26 are arranged around the optical axis 24 on the object surface 25. The photo detector array 26 receives the images of the defects in the dies 2 formed on the optical axis 24. The photo detector array 26 consists of a lot of light-receiving elements 54 (see FIG. 2C) which have respective photosensitive surfaces having a width d1, wherein the width d1 is substantially the same as the width, in the y' direction (the direction vertical to the page space of FIG. 2A), of a line image 59P in the image surface 25. The line image 59P corresponds to the illuminated area 59 on the semiconductor wafer 1. And the number of the light-receiving elements 54 is determined so as to receive the whole line image 59P extending in the x' direction. The positional relations not mentioned above are the same as those in the embodiment shown in FIG. 1A.

Figure 15A:
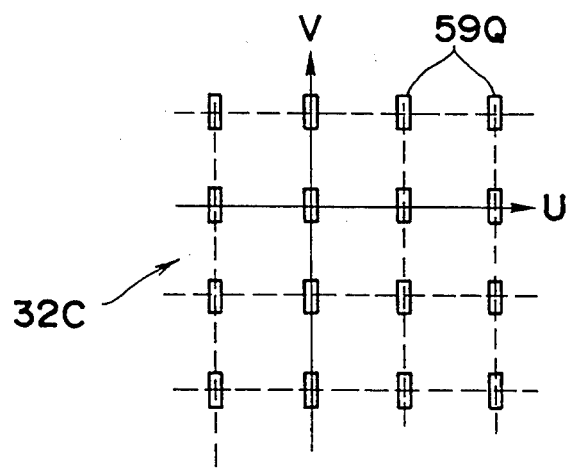
FIGS. 15A to 15C are plan views showing the Fourier transform patterns obtained by executing Fourier transform of the die circuit patterns shown in FIGS. 8A to 8C by means of the second embodiment, shown in FIGS. 2A to 2D of the defects and foreign substance inspecting apparatus according to the present invention.
Figure 15B:
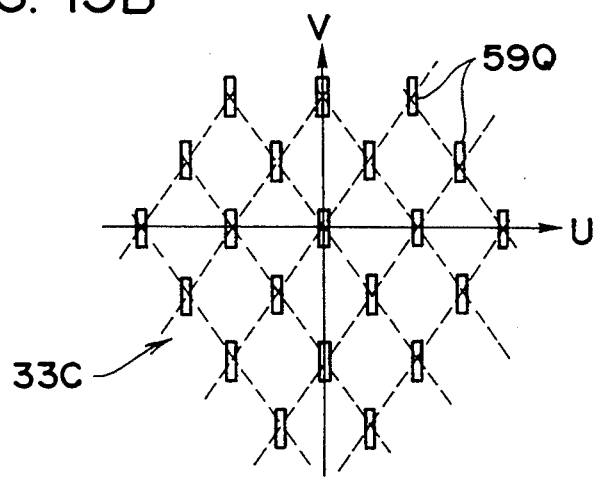
Figure 15C:
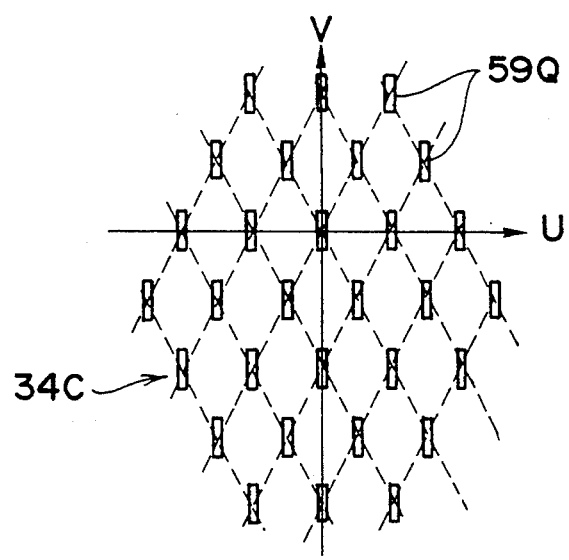

In this embodiment, the Fourier transform patterns 32C, 33C and 34C shown in FIGS. 15A, 15B and 15C, corresponding to the inspected die circuit patterns shown in FIGS. 8A, 8B and 8C, respectively, are formed on the Fourier transform plane 17. Each beam spot 59Q in the Fourier transform patterns 32C, 33C and 34C is a rectangle extending in the V-axis direction. By blocking the normal components in the Fourier transform patterns in FIGS. 15A to 15C by means of the spatial filter 21 and two-dimensionally displaying the output signals from the photo detector array 26 as shown in FIG. 2D, the defect(s) in the dies 2 on the semiconductor wafer 1 can be displayed.

Next, the third embodiment according to the present invention will be described with reference to FIGS. 3A to 3D. In this embodiment, the process invention is also applied to an apparatus for inspecting defects present in the periodical structure of a semiconductor wafer having a lot of circuit patterns. In FIGS. 3A to 3D, components corresponding to those shown in FIGS. 2A to 2D are indicated by the same reference numerals and detailed description thereof is omitted.

Figure 3D:
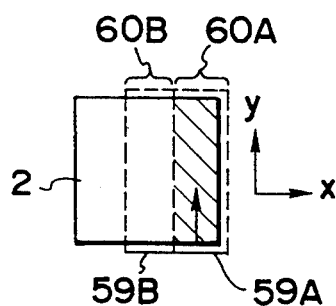
FIG. 3D is a plan view showing the die 2 on the semiconductor wafer 1 shown in FIG. 3A.
Figure 3C:
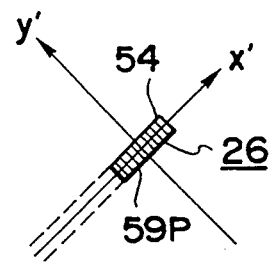
FIG. 3C is a diagram showing the photoelectric detector array 26 shown in FIG. 3A, which is seen from the side of the lens 23.
Figure 3A:
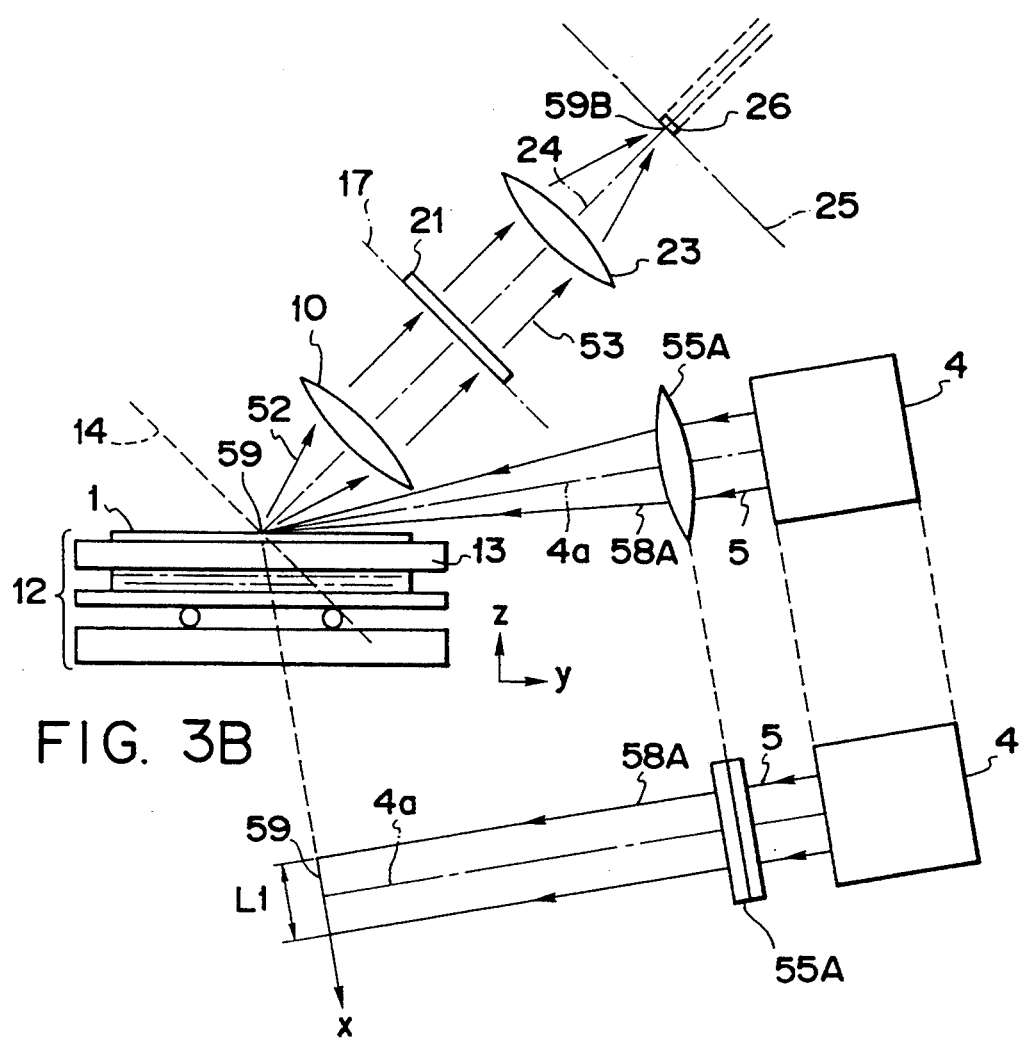
FIG. 3A is a block diagram showing the third embodiment according to the present invention.
Figure 3B:
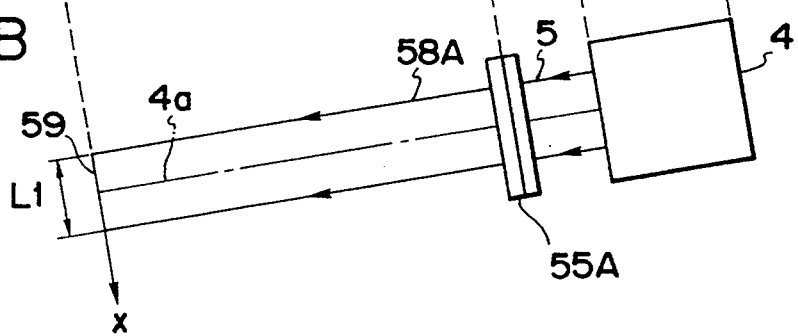
FIG. 3B is a diagram seen from the upside showing a cylindrical lens 55A, the illuminated area on the semiconductor wafer 1, and so on shown in FIG. 3A.

FIG. 3A shows the defect and foreign substance inspecting apparatus of the present embodiment, in which a laser beam from the laser light source (not shown) is converted into the substantially collimated monochromatic beam 5 by the beam expander 4, and the beam 5 travels along an optical axis 4a and is incident on a cylindrical lens 55A. The cylindrical lens 55A has power in the direction in the page space of FIG. 3A and vertical to the optical axis 4a, but does not in the X direction (vertical to the page space of FIG. 3A). A beam 58A emitted from the cylindrical lens 55A is focussed on a linear illuminated area 59 having length L1. The linear illuminated area 59 is part of the rear focal line of the cylindrical lens 55A elongated in the X direction. The illumination area 59 is part of the region on the surface of the semiconductor wafer 1 on which circuit patterns are formed. The optical axis 4a, which is vertical to the page space of FIG. 3A, of the beam 58A to be focussed on the illuminated area 59 slantingly intersects the surface of the semiconductor wafer 1 at an incident angle of about 90°.

In FIG. 3A, the semiconductor wafer 1 is attached inside the chuck 13 which is a part of the two-dimensional parallel displacement means 12. Above the semiconductor wafer 1, the Fourier transform lens 10, the spatial filter 21 and the inverse Fourier transform lens 23 are arranged in the order named slantingly with respect to the surface of the semiconductor wafer 1. In this case, the common optical axis 24 of the lenses 10 and 23 is arranged to cross the optical axis 4a of the illumination optical system on the surface of the semiconductor wafer 1 at an angle smaller than 90°. At the same time, the linear illuminated area 59 illuminated by the illumination optical system has to be included in the object surface (the front focal surface) 14 of the lens 10. Thus, when the beam 58A from the illumination optical system including the cylindrical lens 55A is reflected by the semiconductor wafer 1, the regularly reflected beam and those in the vicinity of the regularly reflected beam, that is, the beams diffracted by the normal circuit patterns on the semiconductor wafer 1, are not incident on the light-receiving optical system including the lenses 10 and 23.

The beam 52 diffracted by the illuminated area 59 on the semiconductor wafer 1 is transmitted through the lens 10, and forms the Fourier transform patterns on the Fourier transform plane (the rear focal surface) 17 of the lens 10. The previously prepared spatial filter 21 is set in the Fourier transform plane 17. The spatial filter 21 blocks the components of the spatial frequency corresponding to the dies 2 without defect(s) in the Fourier transform information obtained by illuminating the dies 2 on the semiconductor wafer 1, but transmits light generated from defect(s) in the inspected dies 2. The beam 53 carrying the information of the defect(s) which is not blocked by the spatial filter 21 is incident on the inverse Fourier transform lens 23. And the lens 23 executes inverse Fourier transform of the light patterns filtered by the spatial filter 21 onto the image surface (the rear focal surface) 25 of the lens 23.

The one-dimensional photo detector array 26 is arranged around the optical axis 24 on the image surface 25 in order to receive the images, which are formed on the optical axis 24, of the defect(s) present in the dies 2 on the semiconductor wafer 1. The rest of the constitution is the same as that of the apparatus shown in FIGS. 2A to 2D.

In this embodiment, as shown in FIG. 3D, the entire die 2 on the semiconductor wafer 1 is illuminated as follows. First, a range 60A is scanned by the linear beam with which the linear illuminated area 59 is illuminated by relatively displacing said linear beam in the Y direction by means of the two-dimensional parallel displacement means 12. Then, the beam with which the linear illuminated area 59B is illuminated is relatively displaced to the position where an illuminated area 59B is illuminated with said beam. And an illuminated range 60B is similarly scanned in the y-direction with the beam with which the illuminated area 59 is illuminated. By repeating the above-mentioned operation, the entire die 2 is scanned with the beam with which the linear illuminated area 59 is illuminated in the same way as the embodiment shown in FIGS. 2A to 2D.

As described above, this embodiment is a modification of the embodiment shown in FIGS. 2A to 2D, wherein the light-receiving optical system is provided along the optical axis 24 and the illumination optical system is provided along the optical axis 4a. The illumination optical system is much slanted with respect to the surface of the semiconductor wafer 1. With said constitution, the intensity of light diffracted by the normal die circuit patterns on the semiconductor wafer 1 and then incident on the light-receiving optical system can be reduced. So, even if the performance of the spatial filter 21 is not excellent, optical noises can be sufficiently reduced.

Incidentally, though, in the embodiment shown in FIGS. 3A to 3D, both the optical axis 4a of the illumination optical system and the optical axis 24 of the light-receiving optical system are arranged slantingly with respect to the surface of the semiconductor wafer 1, one of the optical axes 4a and 24 may be arranged to be vertical to the surface of the semiconductor wafer 1.

Next, the fourth embodiment according to the present invention will be described with reference to FIGS. 4A to 4D. This embodiment is a modification of the embodiment shown in FIGS. 3A to 3D. In FIGS. 4A to 4D, components corresponding to those shown in FIGS. 3A to 3D are indicated by the same reference numerals and detailed description thereof is omitted.

FIG. 4A shows the defect and foreign substance inspecting apparatus of this embodiment, in which the oscillation mirror 46 is revolvably set around the shaft 47 which is parallel with the page space of FIG. 4A. And as shown in FIG. 4B, the substantially collimated monochromatic beam 5 emitted from the laser light source and transmitted through the beam expander (not shown, either) is incident on the oscillation mirror 46. The beam 5 is reflected by the oscillation mirror 46, and then, is incident on a telecentric scan lens 62 as a beam 61.

In FIG. 4A, the effective center of the telecentric scan lens 62 is arranged at a position away from the surface of the semiconductor wafer 1 along the optical axis 4a so that the distance between the effective center and the surface of the semiconductor wafer 1 is the same as the focal distance of the scan lens 62. Thus, a focussed beam 64 emitted from the scan lens 62 is case on the surface of the semiconductor wafer 1. In this case, by oscillating the oscillation mirror 46 around the shaft 47, the position of the focussed beam 64 is shifted in the X direction, wherein the center of the movable range of the focussed beam 64 coincides with the position of the focussed beam 63. Thus, the linear illuminated area 59 on the semiconductor wafer 1 extending in the x-direction and having length L1 is illuminated.

In FIG. 4A, the linear illuminated area 59 is on the object surface 14 of the Fourier transform lens 10, wherein the common optical axis 24 of the Fourier transform lens 10 and the inverse Fourier transform lens 23 crosses the optical axis 4a of the scan lens 62 at the center of the illuminated area 59. The rest of the constitution is the same as that of the apparatus shown in FIGS. 3A to 3D. And also in this embodiment shown in FIGS. 4A to 4D, the defect(s) in the dies 2 on the semiconductor wafer 1 can be inspected with sufficiently small optical noises.

Note that the present invention is not limited to the above-mentioned embodiments. Needles to say, various kinds of constitution and modifications which are concerned with the aspects of the present invention are also included in the present invention.

For example, in the apparatus shown in FIGS. 1A to 1E, the illumination light beam 5 may be slantingly incident on the surface of the wafer 1, as in the apparatus shown in FIGS. 3A to 3D.

Also, in each of the above-mentioned embodiments, if the object to be inspected is a transparent substrate as a reticle, and so on, the light transmitted through the transparent substrate may be inspected by means of the photo detector array 26.

What is claimed is:

1. An apparatus for inspecting defects and foreign substance on an object to be inspected, the object having patterns, comprising:
   a first lens for optically forming Fourier transform images of said patterns;
   a second lens for executing inverse Fourier transform of said Fourier transform images;
   a light source for emitting illumination light;
   an illumination optical system for focusing said illumination light and illuminating a spot of an illuminated area or a linear illuminated area on said patterns to be inspected;
   an optical filter for blocking components of the Fourier transform images corresponding to said patterns without defects from said optically formed Fourier transform images;
   a photoelectric detector for photoelectrically converting images, which are projected by said second lens, of the defects and foreign substance on said object to be inspected; and
   a scanning device for relatively displacing said patterns to be inspected and said illumination light.

2. An apparatus according to claim 1, wherein said illumination optical system illuminates an area around an optical axis of said first and second lenses on said patterns to be inspected, said photoelectric detector has a light-receiving surface for receiving light from said object, and said light-receiving surface is disposed at a conjugate position with respect to said area around the optical axis on the patterns to be inspected.

3. An apparatus according to claim 1, wherein said photoelectric detector has plural light receiving surfaces for receiving light from said object, the size of each light-receiving surface is smaller than the size of the smallest image which is projected by said second lens, of the defects on the patterns to be inspected.

4. An apparatus according to claim 1, wherein said photoelectric detector has a light-receiving surface for receiving light from said object, and the size of said light-receiving surface is substantially the same as the size of a conjugate image, which is formed by said first and second lenses, of the illuminated area illuminated by said illumination optical system on the patterns to be inspected.

5. An apparatus according to claim 1, wherein the optical axis of said illumination optical system is arranged slantingly with respect to the direction vertical to the object to be inspected, and the optical axis of said first and second lenses crosses the optical axis of said illumination optical system on the object to be inspected.

6. An apparatus according to claim 1, wherein the optical axis of said first and second lenses is arranged slantingly with respect to the direction vertical to the object to be inspected.

7. An apparatus according to claim 5, wherein the optical axis of said first and second lenses is arranged slantingly with respect to the direction vertical to the object to be inspected.

8. An apparatus for inspecting defects and foreign substance on an object to be inspected, the object having patterns, comprising:
   a light source for emitting an illumination light;
   an illumination optical system for focusing said illumination light and illuminating a spot of an illuminated area or a linear illuminated area on said patterns to be inspected;
   a detector for detecting light from said object through a lens optical system;
   an optical filter for blocking components of Fourier transform images corresponding to said patterns without defects from optically formed Fourier transform images of said patterns, said optical filter being disposed in a Fourier transform plane of said patterns in said lens optical system; and
   a scanning device for relatively displacing said patterns to be inspected and said illumination light.

9. A method for inspecting defects and foreign substance on an object to be inspected, the object having patterns, said method comprising:
   focusing illumination light from a light source and illuminating a spot of an illuminated area or a linear illuminated area on said patterns to be inspected;
   detecting light from said object through a lens optical system;
   blocking components of Fourier transform images corresponding to said patterns without defects from optically formed Fourier transform images of said patterns; and
   relatively displacing said patterns to be inspected and said illumination light.

* * * * *